(12) United States Patent
Dixon et al.

(10) Patent No.: US 6,663,637 B2
(45) Date of Patent: Dec. 16, 2003

(54) VERTEBRAL DISTRACTION STABILIZER

(76) Inventors: Robert A Dixon, 10577 Durham Pl., Powell, OH (US) 43065; Donald J. Hackman, 3499 Kirkham Rd., Upper Arlington, OH (US) 43221

( * ) Notice: Subject to any disclaimer, the term of this patent is extended or adjusted under 35 U.S.C. 154(b) by 10 days.

(21) Appl. No.: 10/039,509

(22) Filed: Jan. 2, 2002

(65) Prior Publication Data

US 2002/0087163 A1 Jul. 4, 2002

Related U.S. Application Data

(60) Provisional application No. 60/259,349, filed on Jan. 2, 2001.

(51) Int. Cl.[7] ............................................... A61B 17/60
(52) U.S. Cl. ............................ 606/90; 606/99; 606/86
(58) Field of Search ........................... 606/90, 61, 99, 606/102, 86

(56) References Cited

U.S. PATENT DOCUMENTS

| 5,484,437 | A | | 1/1996 | Michelson |
| 5,489,307 | A | * | 2/1996 | Kuslich et al. ............ 128/898 |
| 5,899,908 | A | | 5/1999 | Kuslich et al. |
| 6,080,155 | A | | 6/2000 | Michelson |
| 6,264,656 | B1 | | 7/2001 | Michelson |
| 2002/0013588 | A1 | * | 1/2002 | Landry et al. ................ 606/99 |

* cited by examiner

Primary Examiner—Cary E. O'Connor
Assistant Examiner—Candice C. Melson

(57) ABSTRACT

This invention comprises a device and a method of maintaining distraction and providing tool guidance in the preparation of an intervertebral space for an implant. It provides a means for attaching a tube, to guide tools that will prepare the vertebra for accepting an implant. At any time during the procedure the tube may be removed to inspect or remove debris from the disc space and the vertebral end plates without disturbing the distraction. The system has multiple tube diameters which can be attached to a common flange to increase the dowel size during the procedure without redistracting.

9 Claims, 4 Drawing Sheets

VERTEBRAL DISTRACTION STABILIZER

CROSS-REFERENCES TO RELATED APPLICATIONS

This patent application was preceded by:
Provisional Patent No. 60/259,349 with a file date of Jan. 2, 2001

STATEMENT REGARDING FEDERALLY SPONSORED RESEARCH OR DEVELOPMENT

Not applicable Reference to a microfiche appendix: not applicable

BACKGROUND OF THE INVENTION

Spinal fusions are performed to treat degenerative diseases, deformities, and trauma. These problems generally cause or allow displacement or rotation of a vertebra relative to the adjacent vertebra. The objective of spinal implants is to facilitate realignment and/or fixation of spinal elements for fusion. Clinical studies have demonstrated that surgeries using spinal implants are more effective in providing structure and rigidity to the spine, than surgeries in which implants are not used. The majority of existing spinal implants use metal rods or plates to restrict the relative motion of the adjacent vertebra while fusing takes place. Once the two vertebrae are fused there is no longer a need for the rods or plates which may later cause complications. Bone dowels may be implanted for fusion without rods or plates and remain with the vertebra leaving no foreign material.

DESCRIPTION OF PRIOR ART

A bone fusion, using threaded cylindrical dowel implants, may be performed between two adjacent vertebrae to restore the space originally occupied by a disc. To increase the surface area of contact between the flat vertebral end plates and the cylindrical dowel or the absorbable fixation screw surface, it is necessary to machine partial cylindrical concave surfaces on the flat vertebral end plates to conform to the dowel.

In the prior art a distractor, consisting of a tube with two protruding tangs, was used for initial distracting, maintaining distraction, and acting as a guide during machining and implantation. These tangs may be referred to in the literature as "extended outer sleeves". The tangs are hammered into the disc space to force and maintain distraction. A number of problems are associated with this method of distraction.
(1) The hammering or impacting may cause trauma to the vertebrae, the ligaments, the blood vessels, and the nerves.
(2) Once the tube is in place it cannot be removed until the dowel is implanted. This prevents the surgeon from inspecting the disc space, the thread depth, or the endplate condition.
(3) Since the tangs are tapered 61, any movement of the tube causes a component of the holding force to tend to dislodge the tube.
(4) The tangs do not hold the tube reliably and they allow trapezoidal deformation, especially with the cervical vertebrae, which are smaller than the lumbar vertebrae.
In other designs wedges, paddles, or plugs distract the vertebra prior to inserting the tangs, however the same tube instabilities and vision obstructions remain. A more stable and more versatile system will eliminate these deficiencies.

U.S. Pat. No. 6,080,155 has many similarities to the present patent, however the 155 patent discloses a tube with tangs, which are driven or hammered into the disc space. It does not provide for removing the tube and retaining distraction and it has no clearance undercuts to avoid the vertebral protrusions. These vertebral protrusions are not accurately portrayed in the 155 patent figures. Better representations are shown in FIGS. 5, 6, 12, and 13 of the present patent.

U.S. Pat. No. 5,899,908 discloses a tube with small teeth, which are driven or hammered into the vertebra. Experience has shown that these teeth will not retain the distraction while the tube is guiding the tools inside of the tube. These teeth also do not provide for removal of the tube for inspection while retaining distraction. In the 908 patent the figures do not accurately portray the vertebral protrusions. Better representations are shown in FIGS. 5, 6, 12, and 13 of the present patent.

SUMMARY OF THE INVENTION

The purpose of the present invention is to provide a device and a method to prepare the flat surfaces on the intervertebral end plates to receive a cylindrical implant. This device comprises a distractor, a flange, a series of guide tubes, attachment screws and tools. The distractor is positioned between the vertebral end plates and produces spreading or distraction of the vertebrae. This distraction will assure that the disc space height will be restored. The disc need not be removed before distraction.

The distractor will remove a portion of the disc, a reamer means will later remove the remaining portion of the disc that would interfere with the thread tap and dowel insertion. Once the vertebrae are spread, the flange is placed over the distractor shaft and on to the distractor-centering disc. This disc will insure that the flange is concentric with the distractor. When the flange is in place, attachments screws are placed through the holes in the flange tabs and into the adjacent vertebrae to maintain rigid vertebral spacing while the tooling and implant are in use. The tube assures that the tools will be centered on and parallel to the vertebral end plates and remain fixed during the procedure. This in turn can facilitate removal of an appropriate amount of bone or cartilage material from each adjacent vertebra. The implant can then be inserted through the flange. A length stop is used to set the depths of each tool. After the machining is completed the implant can be guided through the tube and be contained in place with a holding means, preferably a screw thread. These machining and dowel insertion operations are well known to those skilled in the art.

DETAILED DESCRIPTION OF THE INVENTION

In the description "upper" refers to the vertebra nearer to the patients head and "lower" refers to the vertebra nearer the patients feet. It is also understood that "fixed" and "rigid" are relative terms not implying zero measurable motion, but much less motion relative to the adjacent vertebra than before installation of the distraction stabilizer system. For simplification the stabilizer system is described as a cervical stabilizer in one of many conceivable embodiments, however the present invention may also provide devices and methods for cervical, thoracic, and lumbar spinal fusions anteriorly, posteriorly, and/or laterally. That is not to imply that this is the only embodiment within which the stabilizing system can be configured. The components may be fabricated from metal or polymers. Two or more implants may be used in parallel for supporting the vertebra.

Figure 1:
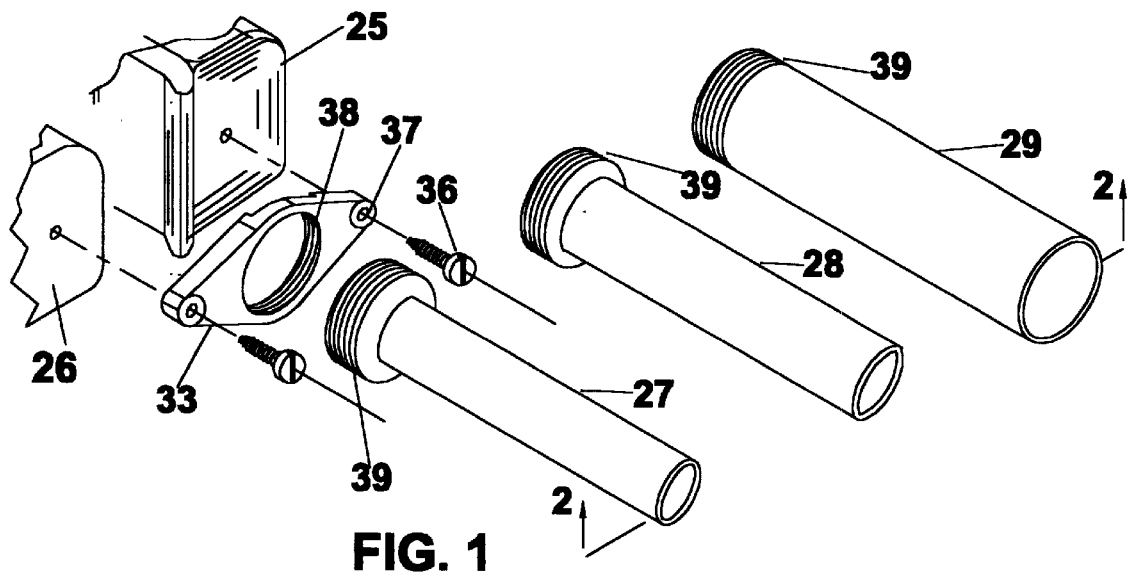
FIG. 1 is an exploded isometric view of the vertebral distraction stabilizer, showing the flange, the attachment screws, and three interchangeable tubes.
Figure 2:
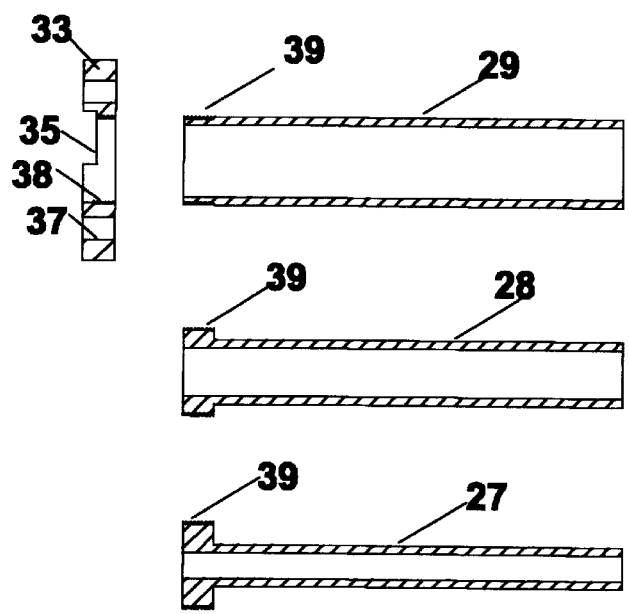
FIG. 2 is an exploded side section view, along the line 2—2 of FIG. 1, of the flange and the three interchangable tubes.
Figure 11:
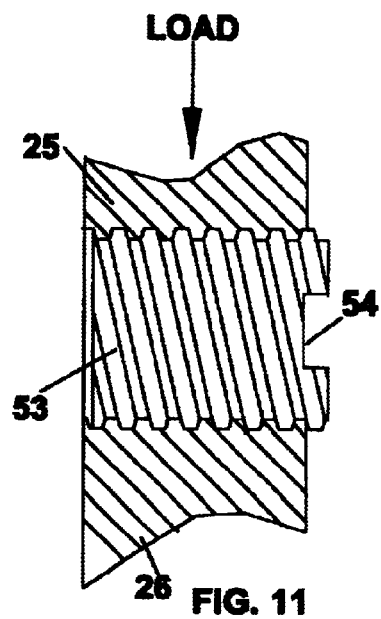
FIG. 11 is a side section view of the implant threaded into the vertebral disc space.

FIG. 1 shows the implant device distraction maintaining flange and the guide tube. FIG. 2 shows the views of three tubes 27, 28, and 29 that attach to the common flange. Unlike stabilizing plates or rods, which stress share or stress shield the implant; this dowel implant, shown in FIG. 11, supports the vertebral end plates and forms a series structure with the vertebra, supporting the entire force of the spine above the upper vertebra. There is no plate or rod sharing the load with the implant. This loading maintains compression between the implant and the machined surfaces of the vertebra. Recent studies have shown that a device that allows the implant to remain in compression will tend to lessen joint separation and increase the fusion rate by reducing the stretching rupture and shearing of the forming blood vessels.

The Herniated Disc

Figure 4:
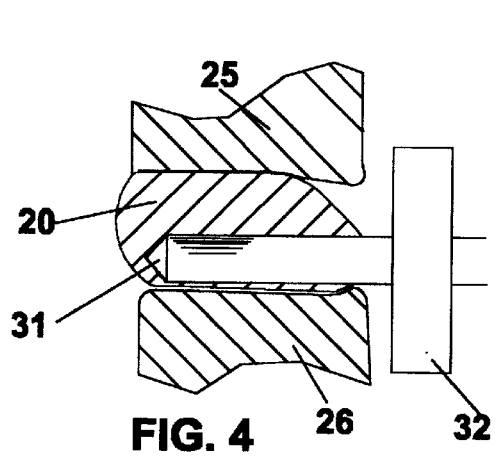
FIG. 4 is a side section view, along the line 4—4 of FIG. 3, of a collapsed disc showing a paddle distractor inserted into the disc space.

A collapsed disc 20 is shown in FIG. 4. When spinal discs rupture or bulge from injury or from degeneration, the space between two adjacent vertebra 25 and 26 decreases as shown in FIG. 4. Frequently the bulging does no harm; but if it compresses against the spinal cord or a nerve it may cause pain, loss of sensation, or weakness. In these situations, when surgery is indicated, it is generally safer to replace the disc with a rigid implant and accept the loss of motion that the disc once provided. The discs are soft and stringy and can be easily removed after distraction, if access is provided to the surgeon. With single-piece tang-distractor tube systems, the tube cannot be removed for inspection without releasing the distraction.

The Vertebral Distractor

Figure 5:
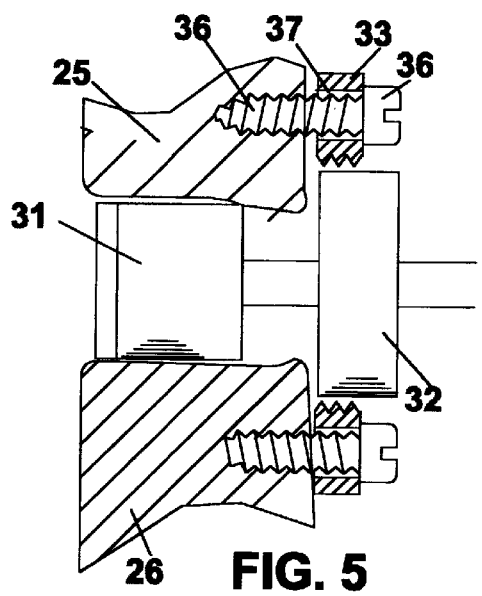
FIG. 5 is a side section view, along the line 4—4 of FIG. 3, of a paddle distractor inserted into the collapsed disc and rotated 90 degrees to spread two adjacent vertebrae, restoring the disc space height. The flange is centered on the distractor alignment disk and fixed to the vertebrae with attachment screws.
Figure 12:
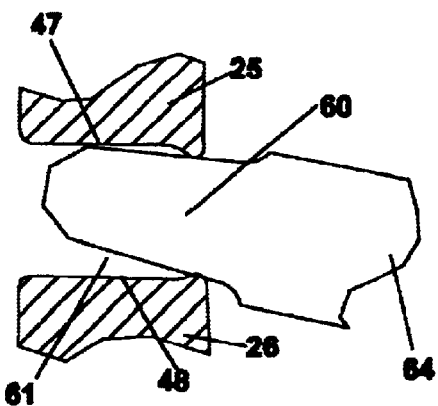
FIG. 12 is a section view of a prior art tube with tapered tangs showing the distractor misalignment.
Figure 13:
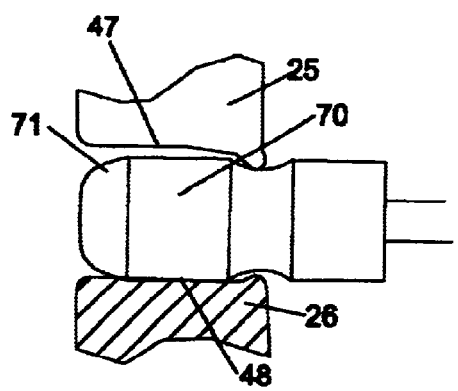
FIG. 13 is a view of a cylindrical plug distractor.

FIG. 4 shows a paddle type distractor 31 inserted perpendicular to the spinal axis. When rotated 90 degrees, as shown in FIG. 5, the disc space is restored to allow for preparation and implantation between two adjacent vertebrae. The distal end of the distractor may have a knife-edge to aid in removing or separating the disc and facilitating placement of the distractor. The distractor has a circular guide disk 32 or other alignment gauging means to align the flange with the vertebral end plates. FIG. 12 shows a misaligned tang distractor 60 as a part of tube 64 as used in previous art. FIG. 13 shows an example of a plug distractor 70 and the tapered section 71. The tang and the plug distractor are forced or driven into place between vertebrae 25 and 26.

The Distraction Stabilizing Flange

Once the vertebrae are spread or distracted, the flange 33 is placed over the distractor stem, shown in FIG. 5, where it is centered over the circular guide disk 32 on the distractor. This insures that the flange is concentric with the distractor axis and centered on a plane midway between the two vertebral end plates. The attachment screws 36 are placed through the flange tab holes 37 and threaded into the adjacent vertebra 25 and 26 to maintain the vertebra's relative position while the tool and implanting operations are taking place. Attaching the flange without the tube in place allows the surgeon to have more working space to install the flange attachment screws. The flange 33 may be made of nonmetals to allow for fluoroscopic viewing.

Figure 6:
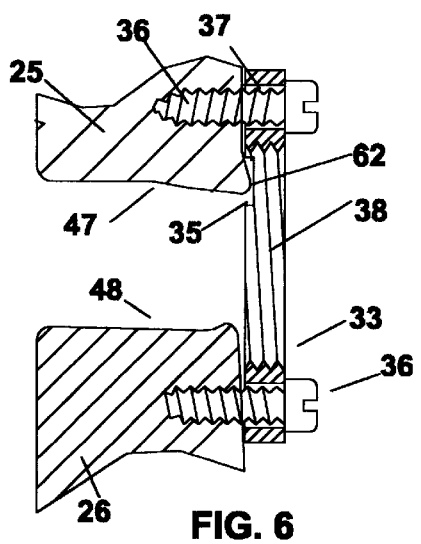
FIG. 6 is a side section view, along the line 6—6 of FIG. 7, of a vertebral disc space with the distractor and the tube removed, showing the attached flange maintaining the distraction. The vertebral clearance notch is shown on the upper portion of the flange. The disc space and vertebral end faces are open and may be inspected by the surgeon.
Figure 7:
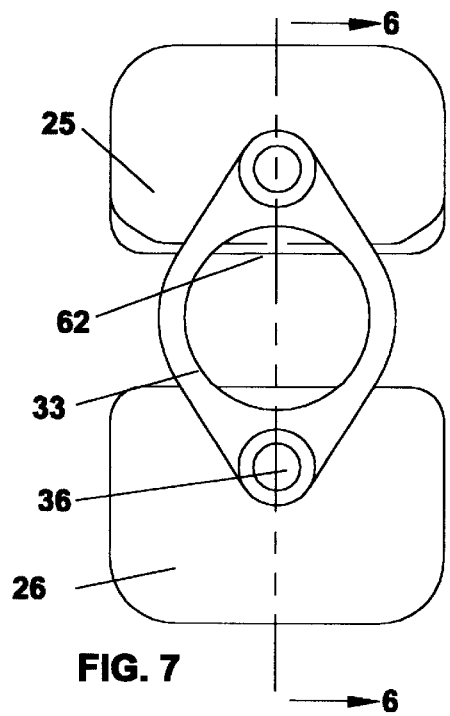
FIG. 7 is an anterior view showing the flange attached, holding the distraction. The disc space, the vertebral end plates, and the vertebral protrusion are visible.

After the flange is attached the, surgeon may remove the distractor. FIGS. 6 and 7, show that the flange opening is not impeded, enabling the surgeon to gain access to a distracted disc space to inspect the disc space and to remove disc or bone pieces. Use of the device of the present invention has demonstrated that poorly formed threads may be hidden from view by the tubes of prior art. No other device gives the surgeon this open access to the disc space. The tube 34 may than be attached to the flange to align and guide the tools, which ream, thread, and install the implant dowel. The tube may be removed before removing the flange, allowing the surgeon to inspect the implant after the implantation.

Flange 33 also allows a clearance notch 35, shown in FIGS. 1, 2, and 6, machined into the flange to clear the front of the vertebral protrusion 62. This will allow the flange to be clamped to the vertebra body 25 rather than against the protrusion. Clamping to the body will add more rigidity and better alignment to the flange and ultimately to the guide tube 34 and the tools.

The Guide Tube

Once the flange 33, shown in FIG. 5, is fixed to the vertebra with attachment screws 36 and the distractor 31 is removed, the tube 34 with thread 39 is threaded into the flange internal thread 38. The tube will guide the tools and the implant, to assure that the reamer 40 and the tap 43, shown in FIGS. 8 and 9, will be centered on the vertebral end plates 47 and 48. This positioning will facilitate removing an appropriate amount of plate and bone from each adjacent vertebra. The machining tools and implant may be inserted through the proximal end of tube 34.

The Vertebra Machining Tools

Figure 8:
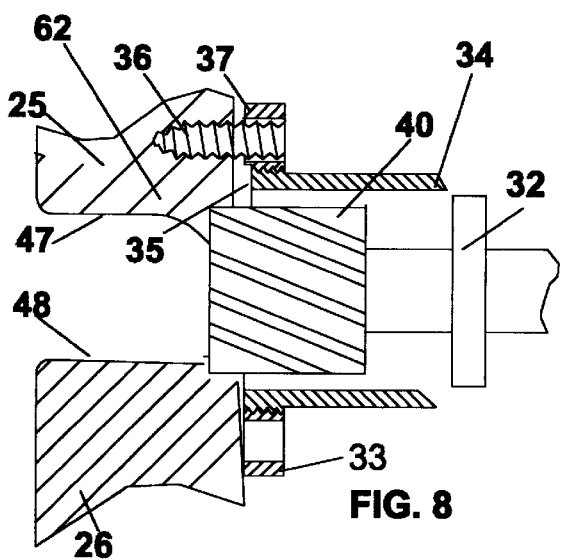
FIG. 8 is a side section view, along the line 4—4 of FIG. 3, of the guide tube attached to the flange and the reamer cutting the vertebral end plate.
Figure 9:
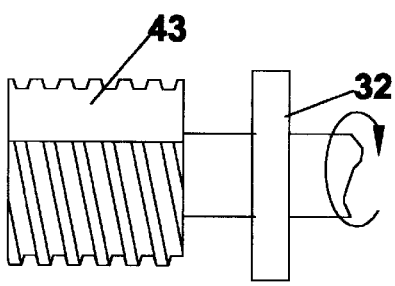
FIG. 9 is a side view of the thread tap and the tool-centering disk.

The tube 34 assures that the tools 40 and 43, in FIGS. 8 and 9, will be centered on and parallel to the vertebral end plates 47 and 48. A reamer 40 is used to cut cylindrical arcs from the fusing surfaces to prepare for cutting the internal threads 42 in the vertebral end plates 47 and 48. The tool guidance tube 34 facilitates removing an appropriate amount from the cartilage and bone of each adjacent vertebra 25 and 26. After the surfaces are machined to the appropriate size and surface finish, a threading tap 43, which will accommodate the selected implant, will cut the internal threads. The machining tools will pass through the matching tube. If incomplete threads 46 require a larger tap, a larger tube may be attached to the common flange, to accept larger tools. The reaming, tapping, and implant insertion operations are well known to those skilled in the art.

The Implant

After the machining is completed, an implant, preferably a threaded bone dowel 53, is threaded into the taped hole. It is installed with a purpose built screwdriver or other installation means inserted in slot 54. The implant may also be fabricated differently to accommodate other driving or inserting means. The implant may have other features, which will hold it to the driving device as it is being manipulated into position for insertion. In the preferred embodiment, shown in FIG. 11, a threaded bone dowel 53 is implanted for fusion across an intervertebral space, following the removal of a damaged disc. Such implants are structurally load-bearing devices, capable of withstanding the forces supported by the upper vertebra 25. The dowel must be inserted before the distraction stabilizer is removed so that the intervertebral space does not close. The implant of the present invention has a thread to maintain the position. The implant 53 must be in contact with the circular arcs, machined into the vertebral end plates 47 and 48. The implant may be fabricated from metal, nonmetals, polymers, biodegradable materials, bioabsorbable materials, allograft or autograft materials. Several sizes of dowel implants will be available from which the surgeon may chose at the time of surgery.

The Method

Figure 3:
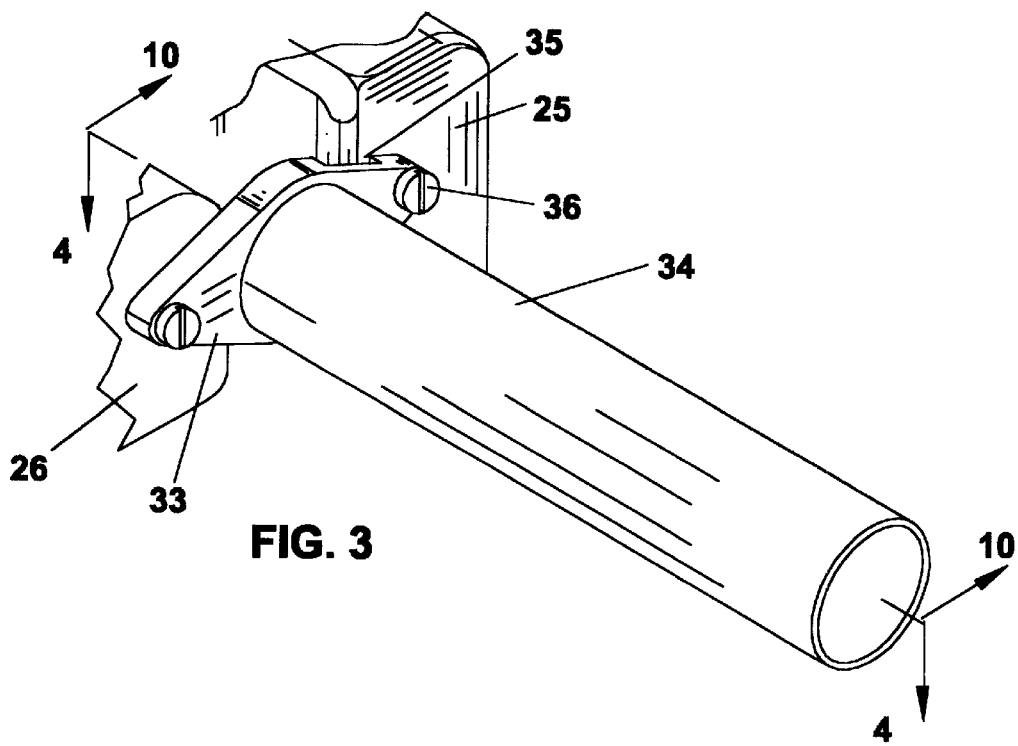
FIG. 3 is an isometric view showing the flange and one tube attached.
Figure 10:
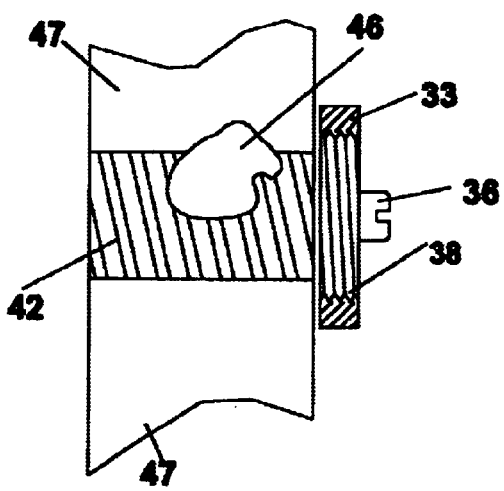
FIG. 10 is a bottom section view, along the line 10—10 of FIG. 3, of the implant showing incomplete threads.

The implantation method allows several variations that will insure a higher rate of fusion success. These include the opportunity to provide more inspections and the versatility of increasing the dowel size, without removal of the distraction. Before the procedure is started the surgeon estimates the size of the dowel required. If necessary some of the disc or vertebral debris may be removed with forceps. The procedure is conducted as follows:

1. The distractor 31, shown in FIG. 4, is inserted between the vertebra 25 and 26 into the collapsed disc space.
2. The distractor 31, if a paddle type, is rotated 90 degrees, as shown in FIG. 5, to spread the disc space to restore the original height.
3. The guide flange 33 is placed over the distractor shaft and centered on the distractorcentering disk 32 to insure the flange and tube will be centered on the vertebral end plates.
4. While centered over the distractor, the flange 33 is fixed to the two vertebrae 25 and 26 with the attachment screws 36 placed through the tab holes 37 and into the adjacent vertebra. The flange and screws maintain the vertebrae relative position while using tools 40 and 43, shown in FIGS. 8 and 9. The screws will insure that the flange will be concentric with the guide tube 34. At the surgeon's option, a starting hole may be drilled in the vertebra, prior to threading the flange attachment screws 36 into the vertebra 25 and 26 as shown in FIGS. 5 and 6.
5. The distractor 31 is rotated an additional 90 degrees and removed from the disc space, with the distraction maintained by the flange, to allow the tools 40 and 43 to be guided into place as shown in FIGS. 5 and 6.
6. The surgeon may inspect the vertebra end plates 47 and 48 and the disc space.
7. The tube 34 is threaded into place on the flange 33, to guide the tools as shown in FIGS. 1, 2, and 3.
8. The reamer 40 is inserted into the tube 34 and rotated to cut cylindrical arcs into the vertebrae as shown in FIG. 8.
9. The tube may be removed to determine if sufficient bone is removed.
10. If more bone depth is needed the next larger tube 28, shown in FIGS. 1 and 2, is attached to the flange 33 and the arcs are reamed with the appropriate larger reamer.
11. After the hole is reamed, the tap 43 is inserted into the tube and is rotated by hand to thread the arcs in the vertebral end faces as shown in FIG. 9.
12. The tube is removed from the flange 33 and the threads are inspected for incomplete or damaged threads 46, as shown in FIG. 10.
13. If the threads are acceptable, the dowel 53 is threaded into the disc space. With the tube removed, the surgeon can measure the depth of the hole and select a dowel of the correct length and he can visually insert it to the desired depth. It can be inserted nearer to the posterior to decrease the lordosis or the anterior to increase the lordosis
14. Once the dowel position is acceptable, the flange 33 is removed by removing the attachment screws 36, to release the distraction held by the flange, allowing the dowel 53 to support the vertebral force. These machining and dowel insertion operations are well known to those skilled in the art.

We claim:

1. A device for distracting and temporarily maintaining the distraction between two adjacent bone segments, which have an upper end and a lower end, in a bone column; and for providing a channel for tool alignment and guidance in preparation for placing an implant, said device comprising:

(a) a flange, having a threaded large hole and two small holes, for placement on and attachment to said bone segments and aligned with said bone segment ends, and (b) a bone segment distractor, having a guide disk alignment gauging section that engages said flange large hole, and (c) one or more guide tubes, open at each end and threaded at one end, said guide tubes removably attach to the said large hole in said flange to provide said channel for tool alignment and guidance.

2. The device of claim 1 where said flange is attached to said adjacent bone segments with self-tapping screws passing through said two small holes.

3. The device of claim 1 where said bone segment distractor is a flat paddle that is inserted into the space between said bone segments, then rotated to cause distraction.

4. A method for distracting and temporarily maintaining the distraction of two adjacent bone segments in a bone column, for providing tool guidance in preparation for placing an implant in the space between the said two bone segments said bone segments having an upper end and a lower end, said method comprising:

providing the device of claim 3;

distracting the said two adjacent bone segments;

placing the said bone segments in the required relationship;

attaching the flange to said bone segments with the self-tapping screws of claim 3;

attaching the guide tube to said flange;

performing machining of said bone segment ends;

removing said tube from said flange;

inspecting said bone segments;

placing an implant into the said space;

removing said flange.

5. A device with a distractor for distracting two adjacent bone segments, m a bone column, in preparation for attaching a flange to said bone segments, said bone segments having an upper end and a lower end, said device comprising:

(a) said flange, having a large hole and two small holes, for placement on and attachment to said bone segments and aligned with said bone segment ends, and (b) said distractor having a circular guide disk that engages and positions said flange large hole.

6. The device of claim 5 where said flange is attached to said bone segments with self-tapping screws passing through said two small holes.

7. The device of claim 5 where said bone segment distractor is a flat paddle, that is inserted into the space between said adjacent bone segments, then rotated to cause distraction.

8. A device for maintaining the distraction between two adjacent bone segments, in a bone column, for providing a channel for tool alignment and guidance in preparation for placing an implant, said bone segments having an upper end and a lower end, said device comprising:

(a) a flange, with a threaded large hole and two small holes, for placement on and attachment to said bone segment and aligned with said bone segment ends, and (b) one or more guide tubes, open at each end with a threaded section at one end, said guide tubes removably attach to the said large hole in said flange to provide said channel for tool alignment and guidance, and (c) said guide tubes with a threaded section that engages said threads in said flange large hole.

9. The device of claim 8 where said flange is attached to said bone segments with self-tapping screws passing through said two small holes.

* * * * *